United States Patent
Kassman

(10) Patent No.: US 7,617,827 B2
(45) Date of Patent: Nov. 17, 2009

(54) DRUG DELIVERY DISPENSER PACKAGE

(75) Inventor: Leon Kassman, Rockville Center, NY (US)

(73) Assignee: Condax LLC, Rockville Centre, NY (US)

(*) Notice: Subject to any disclaimer, the term of this patent is extended or adjusted under 35 U.S.C. 154(b) by 0 days.

(21) Appl. No.: 12/055,450

(22) Filed: Mar. 26, 2008

(65) Prior Publication Data

US 2008/0289634 A1    Nov. 27, 2008

Related U.S. Application Data

(60) Provisional application No. 60/931,408, filed on May 24, 2007, provisional application No. 60/967,163, filed on Sep. 4, 2007.

(51) Int. Cl.
*A61F 6/04* (2006.01)
*A61F 6/06* (2006.01)
*A61F 6/02* (2006.01)
*A61F 5/00* (2006.01)
*A61F 5/44* (2006.01)

(52) U.S. Cl. ............... 128/844; 128/830; 128/831; 128/832; 128/833; 128/842; 600/38; 600/39; 604/346; 604/347

(58) Field of Classification Search ............... 128/844, 128/842, 830, 831, 832, 833, 834, 835, 836, 128/837, 838, 839, 840, 918; 600/41, 38, 600/29; 206/828, 822, 69; 424/423, 426; 428/35.2, 36.8; 222/93; 604/346, 437; D9/734
See application file for complete search history.

(56) References Cited

U.S. PATENT DOCUMENTS

| | | | | |
|---|---|---|---|---|
| 4,872,556 A | * | 10/1989 | Farmer | 222/107 |
| 5,005,695 A | * | 4/1991 | Tennefos et al. | 206/69 |
| 5,433,219 A | * | 7/1995 | Spery | 128/844 |
| 5,896,983 A | * | 4/1999 | Wood | 206/69 |
| 5,927,278 A | * | 7/1999 | Omrani | 128/844 |
| 5,954,054 A | * | 9/1999 | Johnson | 128/844 |

* cited by examiner

*Primary Examiner*—Patricia M Bianco
*Assistant Examiner*—Ophelia Hawthorne
(74) *Attorney, Agent, or Firm*—Gottlieb, Rackman & Reisman, P.C.

(57) ABSTRACT

A container for dispensing fluids, powders, medications, or aerosolized contents in pre-measured amounts at the moment of delivery. The container can be used to apply a condom or condom like device to the penis in the correct-way-on direction. A detachably-attached polymer or latex film, which serves as the vehicle of delivery, and which could be a condom is located at one end and is rolled over the outside of the package which may or may not have a leak proof layer. To dispense the condom on a penis or fit the film on any extremity, the extremity is inserted into the package and by virtue either of such insertion and/or by virtue of flexing the package to fracture an internal frangible membrane. The membrane may be attached to, or a part of a reservoir that is adhered to the inner walls of the package. The flexing action during the condom donning, automatically fractures the membrane thereby releasing its contents onto the exterior and/or interior surfaces of the condom, prior to said detachably-attached condom being released from the dispenser prior to intercourse.

9 Claims, 8 Drawing Sheets

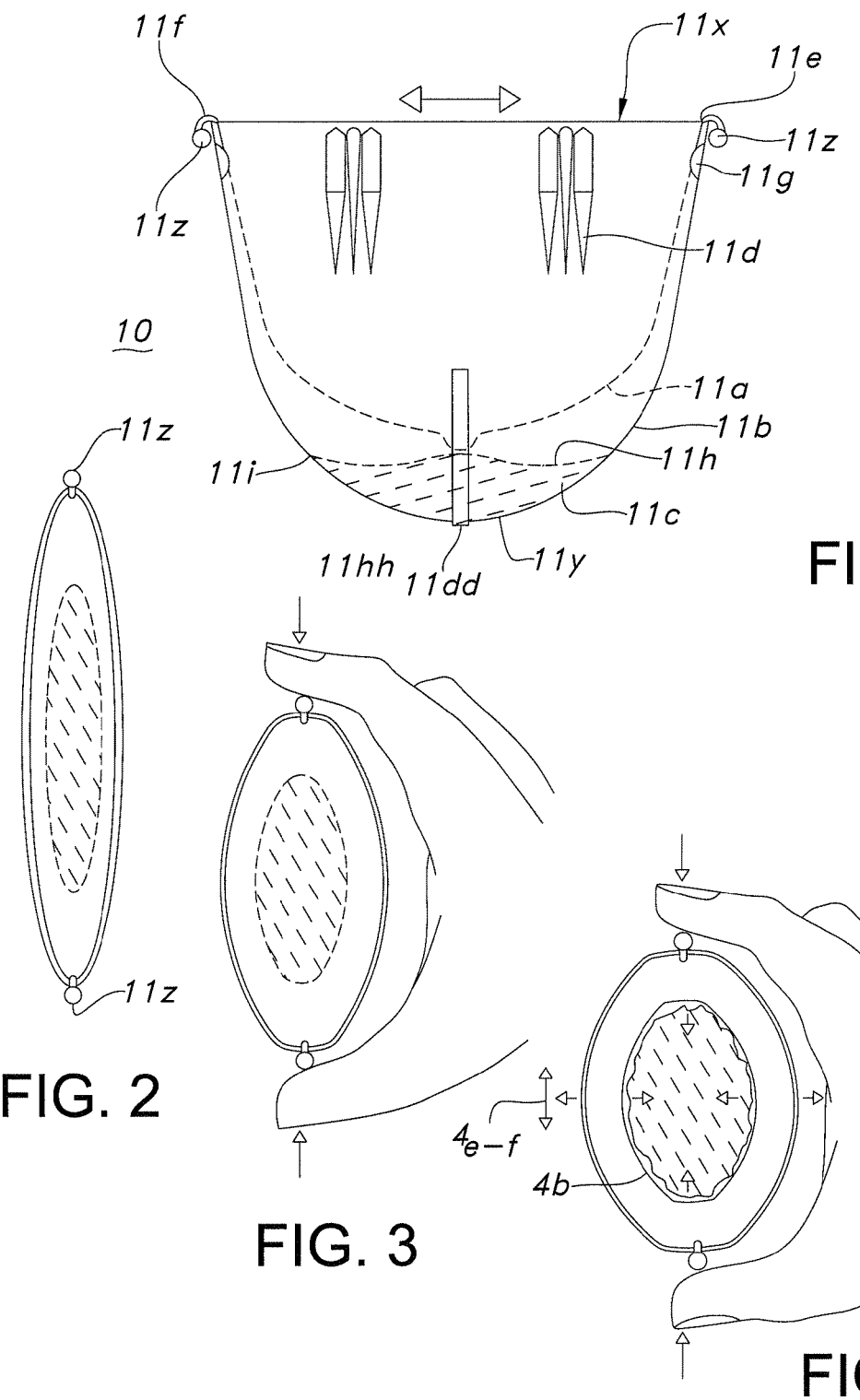

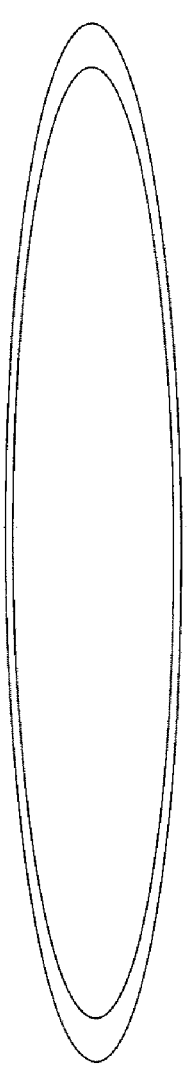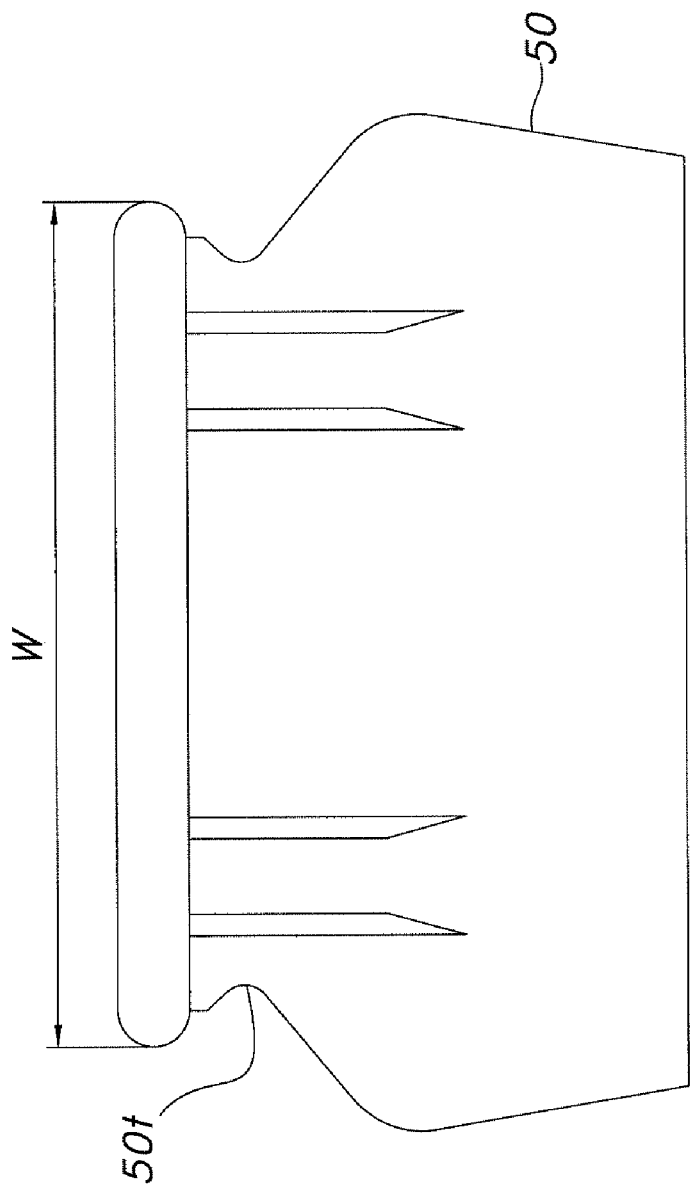

DRUG DELIVERY DISPENSER PACKAGE

RELATED APPLICATIONS

This Application claims priority to U.S. Provisional applications Ser. No. 60/931,408 filed May 24, 2007 and Ser. No. 60/967,163 filed Sep. 4, 2007, all incorporated herein by reference.

FIELD OF THE INVENTION

The present invention relates to an apparatus and method for delivering a fluid, gel, powder or aerosolized preparation to the mucosa of a vagina using a condom. More particularly, the invention relates to an improved condom and package container with a compartment for storing a drug (fluid or powder), where the drug is released from the compartment prior to intercourse.

BACKGROUND OF THE INVENTION

In many instances it is desirable to coat a substance on the mucosa of a person's vagina prior to intercourse. The substance may include, for example, a lubricant, a spermicidal preparation, a disinfectant, or combinations thereof. However, other than various conventional means of inserting non-petroleum based lubricants, there are no means disclosed in the prior art where additives currently placed either within the packaging and which become directly exposed to the condom itself are held as a 'dose' within the packaging but away from the condom itself. Similarly there are no means of separating the condom completely from the contents of any fluid or powder that may be introduced into the packaging for the purpose of lubricating or treating the condom in any manner. Therefore, in the conventional and existing method, due to the migration action of most silicone and/or water-based lubricants, once the fluid is introduced, in time, the fluid covers all surfaces, including most of the inter-rolled dimensions of the condom. This spreading effect may, among other characteristics, expose the fluid to the continual leaching of proteins from the condom itself and this condition or others may result in the diminishment of the originally conceived reason for the lubricant or additive. What is needed is a means of separating the condom from the fluid until the moment the condom is used and then that means should permit the condom portion exposed to it to be saturated by the fluid prior to the condom being detached and used during intercourse.

Some background art is described below.

U.S. Pat. No. 4,840,187 of Brazier which describes a rigid, cylindrical tubular container to dispense rigid male urine collection sleeve, not a flattened closed container openable by pressing upon the side edges corresponding to the major axis of the open end of the container, as noted in the present invention.

Brazier '187 discloses a sheath applicator for directing a steam of urine. Thus the single sheath is open at the distal end and not closed as in a condom. In addition, the tubular casing does not conform to the shape of a condom, has a flexible liner casing which is exposed by side openings to permit adjustment of the flexible liner casing on the penis. Strip 12 therein is designed to expose an adhesive so when the sheath is rolled over the penis, the end of the sheath can be cemented to the base of the penis.

U.S. Pat. No. 4,696,095 of Elenteny has peel away multi-layered gloves which are peeled away one at a time. This arrangement is not suitable for use as a condom, as it lacks the leak proof layers in between the various layers of gloves.

Various devices have been made for releasing a single glove from a vacuum chamber. Wood in U.S. Pat. No. 5,269,405 describes a package for dispensing one or more gloves from a nested plurality of gloves, wherein a pump creates a vacuum to inflate the gloves in an open expanded state.

Wood '405 also discloses a container for sequentially dispensing a single glove from a plurality of gloves placed inside each other, wherein a vacuum holds the plurality of gloves intact in an open position for insertion of a hand therein.

Wood '405 discloses a dispenser for gloves which are stored in a layered condition within a container and a vacuum is applied. Each glove can be removed without disturbing the vacuum. Each glove has the open end pulled around the outside of the container with each succeeding glove layered on top of the preceding one. Adhesive is employed to maintain a seal. To remove a glove the open edge of the glove is pulled away breaking the vacuum surrounding the glove, thus easing the removal of the glove. This is a far different arrangement from the present invention.

Wood in U.S. Pat. No. 5,456,354 describes a package dispenser for garments such as one or more gloves or condoms, from a dispenser which is shaped like the garment to be dispensed.

U.S. Pat. No. 3,695,493 of Karr, disclosing an apparatus for alternately donning and removing a single glove within a vacuum chamber, U.S. Pat. No. 4,069,913 of Harrigan for a package for donning a single surgical glove and U.S. Pat. No. 4,889,266 of Wight for an apparatus which removes a single glove from a disposable single use package.

Other related patents include U.S. Pat. No. 685,574 of Conboie which shows a hand-shaped case, but this patent is for a less related use in mortuaries. U.S. Pat. No. 1,938,685 to Breulis shows a somewhat bulb-shaped cavity for applying a surgical glove. The cuff of the glove is stretched over the opening of the cavity. U.S. Pat. No. 2,741,410 to Violette shows a rack for removing gloves that may be wall mounted.

U.S. Pat. No. 2,886,824 to Smith shows a rubber glove having a tapered wrist shape. U.S. Pat. No. 3,852,826 to Schindler shows a surgical glove which is sterilized using radiation. U.S. Pat. No. 4,186,445 to Stager shows a glove having a mylar outer coating and a polymer foam inner coating. U.S. Pat. No. 4,310,928 to Joung and U.S. Pat. No. 4,851,266 to Momose show talc free surgical gloves. U.S. Pat. No. 4,696,065 to Elenteny shows a single peel-away multi-layer glove. No powder is used between the layers. This glove has a slight taper at the wrist portion.

U.S. Pat. No. 5,224,221 of Richardson describes a single glove which is two layers, one inside the other, with the space between them evacuated.

Various devices have been made for packaging condoms. Wood '405 describes a package for a plurality of condoms, wherein the condoms are nested within a tubular package having an open end and a closed end, wherein a pump creates a vacuum to inflate the condoms in an open inflated state. Wood '354, noted above, describes a package for a plurality of condoms which specifically describes a removable layer between each of the condoms, to maintain a sanitary condition for each of the condoms before use.

U.S. Pat. No. 5,136,825 of White for an apparatus and method for compacting condoms in a pleated package and U.S. Pat. No. 4,867,176 of Lash for a vacuum formed package for a female condom (See FIG. 16 therein) are among prior art patents related to condom manufacturing.

U.S. Pat. No. 4,638,790 of Conway describes a rolled condom which is adhesively adhered to the skin of a male user.

U.S. Pat. No. 5,316,019 of Jones described an annular applicator which functions as a package for a condom.

U.S. Pat. No. 5,267,575 of Hrisko describes a dispenser for an individual condom, wherein the condom is inflated before each use by blowing air through the dispenser to inflate the condom before donning. However, Hrisko '575 only describes an applicator for single condom, which must be inflated by the user blowing air into the dispenser before each use.

U.S. Pat. No. 4,987,905 of Broad describes a "no hands" application for a condom, wherein a pair of strips is moved to release the condom.

U.S. Pat. Nos. 4,961,734 and 6,918,392 both of Kassman disclose a condom detachably attached to a plastic 'package' device and show the attached condom in each to be in contact with any fluid or lubricant that had been packaged along with the condom initially. Neither show any means or method of holding the lubricant preparation in a separated reservoir as contemplated by the present invention.

U.S. Pat. No. 5,181,652 of Tanttu and U.S. Pat. No. 7,063,211 discloses the means and method of partially perforating a substrate film in such a manner so as to make the film frangible with the application of further manual force.

U.S. Pat. No. 6,547,468 of Gruenbacher, discloses using a frangible and permeable reservoir or 'cell' containing any 'active' ingredient situated within an impermeable outer covering to deliver a pre-measured amount of the ingredient when the user provides a certain amount of hand pressure to fracture the internal seal is particularly relevant to the present invention. Gruenbacher does not disclose or envision a detachably attached elastic membrane such as a condom to be assembled to the applicator.

SUMMARY OF THE INVENTION

In view of the above it would be advantageous to provide a disposable dispenser for a single use condom in which a predetermined amount of fluid or powder is held in a reservoir separate from the condom, until the moment the condom is dispensed, at which time the fluid or powder is released.

In as much as conventional latex or non-latex condoms are donned, they may also be referred to as garments. And, it is an object of the present invention to be able to don other garments which may not be configured as a conventional condom.

It is therefore a further object of the present invention to provide a package dispenser for dispensing one or more garments sequentially from a garment-shaped partial vacuum container.

It is yet another object of the present invention to provide a garment dispenser that does not include a vacuum container but instead only partially conforms to the garment within.

It is yet another object of the present invention to provide a garment dispenser that may or may not include a vacuum container but does include a frangible membrane attached between the longer members of the dispenser.

It is yet another object of the present invention to provide a garment dispenser that may or may not include a vacuum container but does include a frangible reservoir attached to the dispenser's interior walls proximate to one open end of the dispenser and thus suspended and firmly attached, can be filled with a fluid or powder.

It is a further object to provide a garment-shaped package with a releasing means including a thin continuous ribbon.

It is a still further object to provide a garment-shaped package where a multiplicity of garments are held with a means of releasing said garments in the form of a thin ribbon detachably-attached to each garment.

It is yet another object to provide a garment package with an annular releasing means.

It is yet another object to provide a container with a neck opening of a garment package which is tapered inward so that when the plastic is pulled off, the garment easily rolls off the package and onto the penis.

It is yet another object to provide a garment dispenser which includes a flexible non-elastic garment shape on the inside of the plurality of garments which is sealed within the package in order to provide a leak-proof, air free area for increased shelf-life or storage life of the garments.

It is yet another object to provide a leak-proof layer in between each garment.

It is yet another object to provide a plurality of garments wherein there is provided an outermost garment shape which constitutes a leak-proof layer, for the purpose of shaping all the garments.

It is yet another object to provide a garment package with an opening which is flared out to prevent unwanted releasing of the garments.

It is yet another object to provide a garment dispenser package with an opening which is tapered in to aid in the releasing of each garment.

It is yet another object to provide a garment package with a mechanical attachment for pulling a release tab, to allow for hands-free or automatic releasing of the garments.

It is an object of the present invention to provide a condom or condom package dispenser which has an inner shape which forces a condom to expand and conform to the proper position to allow easy donning.

It is also an object of the present invention that the dynamic action of the dispenser when squeezed open as part of the condom donning or garment donning process also causes the frangible membrane to perforate thus releasing the contents of the reservoir onto the tip of the garment; and through migration or aerosol action, the contents of the reservoir come into contact with the unrolled portion of the garment, glove or condom.

It is also an object of the present invention to provide a dispenser for dispensing one or more condoms, or packages of condoms, sequentially from a container.

It is a further object to provide a condom shaped package dispenser with a releasing means.

It is a still further object to provide a condom-shaped package dispenser with a hermetically sealed layer between each condom.

It is another object to provide a dispenser which permits a convenient instant-on one-hand-only method of donning condoms.

It is a further object to provide a condom package dispenser which is flattened for convenient storage.

It is yet another object to provide a condom package dispenser wherein the condoms in the package are stored in a relaxed shape, so that when the dispenser is opened for use, a partial vacuum in the hollow tip causes the plurality of condoms to expand into the proper shape. In another embodiment of the present invention the attachment of the membrane across the inner walls of the dispenser replaces the hollow tip and momentarily, prior to fractioning, forms a partial vacuum with the condom detachably-attached at the opposite end in a manner that draws the condom toward the frangible membrane so that, upon perforating, the condom is instantly exposed to the fluid of powdered contents of the reservoir attached to and below the frangible membrane.

It is yet another object to provide a dispenser with a neck opening which is flattened so that when the neck opening is squeezed; a partial vacuum is formed by the increase of volume within the closed interior of the condom shaped dispenser.

It is yet another object to provide a condom package dispenser with a leak-proof layer in between each condom.

It is also an object of the present invention to improve over the disadvantages of the prior art.

It is a further object of the invention to provide a pre-measured amount of medication as a unit-dose directly to a vehicle of spreading the medication within the same package thus eliminating the need to apply said medication in two stages while making certain that the amount of the dose is uniform from application to application.

It is a further object of the present invention that the shape of the package can be constructed to roughly conform to any human extremity or body part capable of being molded into the package shape.

It is a further object of the invention that said package delivery system can be modified to deliver medication, microbicides, fertility treatments, lubricants, lotions, fluids, powders, sprays, or aerosolized contents to humans, animals, and/or pets. Alternatively, it is an object of the invention that the package be modified to deliver a film container to the animal, pet or human for the purpose of collecting a sample of fluid, residue, exfoliation, or detritus.

It is a further object of the invention that said package delivery system can itself serve as a means of supporting any digit or body part either fully or partially inserted into it by having externally applied strapping or adhesive members attached to the package exterior surfaces whose purpose would be to secure same to the inserted part.

It is also envisioned that the package may, itself, be configured so that multiple similar packages may be stacked one atop another, with sufficient means to separate the individual packages while protecting the internal contents so as to permit the packages to be sold in conveniently dispensed multiples.

In keeping with these objects and others which will become apparent, the present invention includes a shaped container package dispenser for dispensing at least one elastic expandable condom or, sequentially, a plurality of condoms. The condom or condoms are dispensed in such a dynamic manner, such that at the moment of dispensing, the outer surface of the condom becomes covered by the fluid or powder that had been separately held within an expandable, frangible membrane topped reservoir, which is attached laterally to the inner package walls and distal to the part of the dispenser package to which the condom was detachably-attached.

In the preferred embodiment, a package dispenses one or more condoms directly onto a penis. The package includes a flexible container made from any substance and shaped having the general configuration that enables it to roughly conform to the general shape of the penis. Said flexible container which forms the body of the dispenser may have a closed end distal from the end to which a condom is detachably attached or it may have an open end sealed by a membrane capable of being torn or perforated by the dynamic action of squeezing the dispensers naturally resting opposing end toward each other at the moment of dispensing so as to cause its longer side member to deflect from one another proportionally and with such action perforating or tearing the frangible membrane attached within the dispenser so as to release the fluid or powder that had, till that moment, been held separately and not in contact with the condom. This action could also contribute to or cause said fluid or powder to spread and migrate on to the surfaces of the condom closest to the frangible membrane's position. The fluid held within the reservoir shall be held at a pressure only slightly in excess of the pressure at sea level. Said pressure shall be used to propel the fluid from the reservoir onto the condom. The frangible membrane shall be tested so that it will function properly and be unaffected by fractioning either by atmospheric pressures 5000 feet above or below sea level or by temperatures of 33° F. to 135° F.

In another embodiment for dispensing elastic expandable garments from a package, the package dispenser container of the present invention may also be used for donning condoms from a condom-shaped package which folds flat for storage.

In summary, the present invention relates to a package dispenser for one or more garments such as a condom or a glove. More particularly, the present invention relates to a package dispenser, wherein a user dons one or more garments sequentially from said vacuum packed garment-shaped container that forms a partial vacuum at the moment of dispensing either from the juxtaposition of the contents to the bottom of the then partially sealed dispenser or by interacting with the frangible membrane whose then non-fractioned surface acts to maintain the partial vacuum.

The present invention also includes a condom-shaped package dispenser for sequentially dispensing at least one elastic expandable condom, from a dispenser package.

In the preferred embodiment, the condom is preferably nested within the package and is maintained in the package in a flattened, partially unrolled state. The user squeezes the flattened package to spread open the end on to which the condom was detachably attached, breaks an air tight seal automatically releasing an air tight layer from around the condom, so that the condom is opened for donning when the condom dispenser is inserted over the skin of the male for use. Simultaneous with said action the action of squeezing the lateral opposing ends of the dispenser toward each other causes the frangible membrane, attached to and within the dispenser immediately beneath the condom, to fraction or tear along pre-engineered perforation lines. This causes the fluid or powder contained within the reservoir to disperse and spread over the external surfaces of the condom closest to it and to migrate toward the rolled end of the condom covering its exterior surface at least as far as the condom had been initially unrolled when it was at rest within the package dispenser. One advantage of this embodiment is that the user is not able to mistakenly don the condom inside out.

In the embodiment where the frangible membrane and the reservoir attached to it form the distal boundary of the dispenser, it will not be designed to house a plurality of condoms and will not be constructed with inner seals separating each condom layer.

In another embodiment the action of applying the condom releases the fluid from the reservoir where the fluid had been maintained under pressure.

In another embodiment the action of applying the condom releases the fluid which is exothermic and therefore warms the condom/garment that was detachably attached to the dispenser.

In another embodiment the dispenser with the garment attached is used only to treat the male. In this case the frangible reservoir is attached at the top open end or, alternatively, at the open end if the dispenser has a closed end. Upon perforating the reservoir compartment, the fluid or powder within the reservoir is then dispersed on the inside of the condom as a treatment for the male. This embodiment where the reservoir is reversed so as to release its contents on the inside of a garment when the frangible membrane is torn during application could be used to treat human extremities such as the fingers and the penis.

In another embodiment the dispenser is fitted with two reservoirs, one to disperse the fluid/powder on either side of the detachably attached garment, without the contents of either compartment coming into contact with each other.

In another embodiment the dispenser is used as it would ordinarily be used during intercourse with the reservoir situated to disperse fluid/powder on the exterior of the condom/garment. However the male does not insert his penis. Instead, the woman, using her fingers, activates the dispenser thus fractioning the reservoir. Then she can either, fit her fingers or a penis-shaped rod into the condom and use the condom to apply the fluid to her own vagina.

In another embodiment, one condom is dispensed from a plurality of condoms and the remaining condoms remain in an open state. This way, when the user desires to use a condom at a later time, the user can release a tab to release a next innermost seal from against the next innermost condom, readying the next innermost condom for use.

The inside of the condom package dispenser of the preferred embodiment is condom-shaped, so that the condom may be expanded in the proper state and condition.

Another embodiment provides a plurality of individually sealed single condom packages in a partially unrolled state to facilitate donning, which packages are removable from each other by a tear seal.

In summary, the inside of the package dispenser for dispensing one or more condoms is condom-shaped. The package dispenser folds flat for storage. There may be a hermetically sealed leak-proof layer in between each condom. This provides extra cleanliness for the inside of the innermost condom that would otherwise be exposed to the outside air. The user dons one or more condoms sequentially from the condom-shaped container. The shape of the dispenser allows condoms to be donned quickly and easily, because the condom shape, when squeezed at the open neck end, forces the condoms to expand and conform to the proper position within the interior of the dispenser.

BRIEF DESCRIPTION OF THE FIGURES

To further satisfy the recited objectives, a detailed description of typical embodiments of the invention is provided with reference to appended drawings that are not intended to limit the scope of the invention, in which:

FIG. 1 is a front view of a condom within a condom dispenser, constructed in accordance with this invention.

FIG. 2 is a top view of the condom package.

FIG. 3 is a top view of the condom package with a hand applying pressure to it to partially open the condom package.

FIG. 4 is a cross sectional view of the condom package in its fully opened position.

FIG. 15 shows a side view of an alternate embodiment similar to the embodiments of FIGS. 6 and 7.

FIG. 15*a* shows an end view of the enclosure used in the embodiment of FIG. 15;

DETAILED DESCRIPTION OF THE INVENTION

Figure 5:
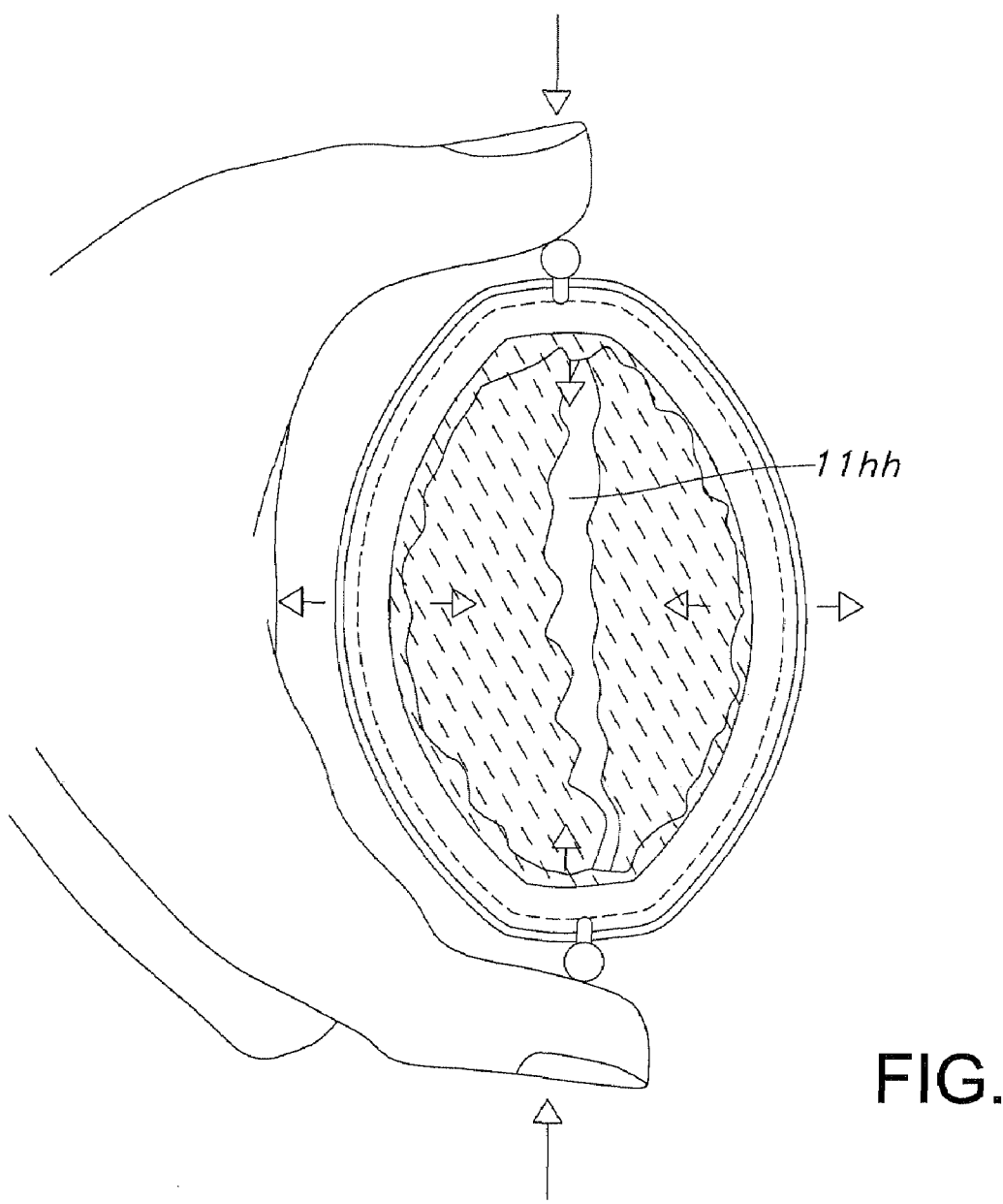
FIG. 5 is a close-up view of the condom package in its fully opened position which shows the reservoir breaking at the perforated seam.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The United States Department of Health, Food and Drug Administration (FDA) mandates that condoms be manufactured to prevent pregnancy and to prevent the transmission of sexually transmitted diseases (STD's) from the mixture of bodily fluids between sexually active persons. Pursuant to 21 U.S.C. §360(c)(a)(1) (2007), FDA regulations classify medical devices in a hierarchy of classification standards, namely, Class I for medical devices which require general controls in manufacturing, Class II for medical devices which also require performance tests, and Class III, for medical devices which require FDA pre-market approval. The FDA has classified the condom as a Class II device under 21 C.F.R. §884.5300 (2007). The condom must be subject to rigorous performance tests, such as air burst tests, to certify that the condoms are sealed from leakage.

The FDA utilizes the manufacturer's standards of the American Society for Testing Materials (ASTM) entitled "Standard Specification for Rubber Contraceptives" (Condoms).sup.11—Designation: D 3492-83 for quality control of leakage defects, wherein the acceptable quality level for leakage is 0.4 percent, that is, not to exceed 4 leaking condoms per 1000 is tested. The FDA's sampling inspections, pursuant to 21 C.F.R. §800.20 (2007), are based on the tables of MIL-STD-105 E which is the military sampling standards in "Sampling Procedure and Tables for Inspection by Attributes", dated May 10, 1989.

Among the tests for condoms include the Air Inflation Test, adopted in 1994 by U.S. inspectors, which includes inflating condoms, checking their elasticity, whereby experts determine the quality that keeps a condom intact during intercourse.

As noted in "How Reliable Are Condoms?" Consumer Reports, May 1995, pp 320-324, latex condoms are produced by dipping a cylindrical form in liquid latex and heating it. Machines shape and trim the condoms ring; then new condoms are washed and aged for a number of days, during a "curing" that lets the rubber complete the chemical actions that strengthen the latex. The final steps are rolling and wrapping individual condoms.

Industry standards standardize on a width of no greater than 54 millimeters,—about 2⅛ inches, to prevent slippage. However, both width and length dimension requirement have been changed to comply with the 2005 FDA (510(k)) approval of Sadlo's U.S. Pat. No. 5,857,466 calling for a multiplicity of condom sizes. The minimum length is 160 mm, roughly 6⅓ inches.

Since 1987, the U.S. Food and Drug Administration has allowed condom boxes to list all the diseases condoms help avert. More recently, the FDA advised a condom manufacturing company that because the disease-prevention message is so important, manufacturers should also print a disease prevention message on the wrappers of individual condoms.

Since 2004, when the Center's of Disease Control (CDC) issued its guidance concerning observations about how the spermicide non-oxynol 9 was demonstrated to be causative in abrading certain user's vaginal mucosa, many condom companies no longer use the spermicide but still use water based or silicone based lubricants that are added directly to the condom during the condoms traditional packaging within cellophane of the FDA preferred silver backed foil wrapper.

FIG. 1 illustrates a condom package 10 constructed in accordance with this invention. The package 10 includes a hard but flexible container 11b. The material of container 11b should be such that it can remain in a fixed position, but upon the application of force, flex or bend with that force. Upon release of the force, the material should return to its original position. For example, the container 11b may be made of cardboard or plastic material. Generally speaking, the container 11b has a curved shape terminating at one end with a mouth or opening 11x between two ends 11e and 11f.

Disposed within the container is a condom 11a. The container 11b, is preferably sized so that it is slightly larger than that of the condom 11a. In different embodiments, the container may be different sizes. Importantly, the container 11b further contains a reservoir 11c of a suitable medicinal composition in the form of a liquid, gel or powder. If necessary, the composition may be aerosolizable. The reservoir 11c is preferably formed between a portion of the container, such as its closed end 11y and a membrane 11h. The membrane 11h is peripherally fixed or attached to the inner wall of container 11b. The connection between the membrane and the container can be made in a number of ways, including but not limited to: an adhesive bonding, sewing, welding or friction.

The container 11b includes at least one support strut 11d. The support strut 11d is provided at the base of the container to maintain the shape of the container while the condom is attached. A similar strut 11dd is provided at the tip of the container 111b as well.

The distance between ends 11e to 11f should be long enough that the condom fits securely, but not so long as to stretch the condom during storage. Such stretch would cause deterioration of the condom material over time. Typically this distance may be about 50-54 mm.

The condom 11a terminates with an open end (not shown for the sake of clarity) that stretches over and wraps around the mouth 11x and is rolled up in an annular ring 11z.

Devices that enable the donning of a condom or the delivery of an active agent or medicinal ingredient from one partition to another are already practiced art in the field of contraception, cosmetics, or medicine. The present invention is distinguished from these devices because it accomplished the transfer more easily and, in one preferred embodiment, the partition membrane holding the active ingredient 11c, itself, forms the lower boundary of the applicator device or dispensing package and, therefore, becomes both a reservoir and an application vehicle. For this purpose, the membrane 11h made from an elastomer or other similar materials whose properties and characteristics are preferably consistent with the performance and storage requirements of latex condoms (should a latex condom be used as the delivery vehicle).

In one embodiment, the membrane 11h is provided with a line 11hh that is either frangible or is rupturable. The line may be implemented by providing the membrane in several sections that are thick and are joined by a thinner region defining line 11hh. Alternatively, the line 11hh is obtained by joining the sections of the membrane using a suitable means such as RF, heat or chemical bonding. The thicker sections, e,g, 11hhh maintain their integrity except when the applicator or delivery package to which it is adhered is either manually flexed so as to change the 'at rest' geometry of the reservoir 11c or by membrane 11h being fractured by the forceable insertion of an insertion tool or via the insertion of any human digit or other structure such as an erect penis. The 'at rest' geometry of the reservoir 11c and the package 10 is shown in FIG. 1. The container 10 is used as follows.

In order to dispense the condom 11a and the contents of the reservoir 11c, the two buttons 11z are compressed manually toward each other, gradually as shown in succession in FIGS. 2, 3 and 4. Typically the container 1b is structured so that an individual's hand exerts at least 5 ft./lbs.and as much as 15 ft./lbs. of compressive/flexing pressure. As a result, the membrane 11h fractures as shown in FIG. 5. If a line 11hh is provided then the fracture will occur along this line.

The present invention is also distinguished by one of its preferred embodiments having a detachably-attached condom or other agent distributing vehicle, pre-assembled to it in such a manner that when the ingredient in reservoir 11c which had been kept separate by virtue of the membrane 11h, is fractured after the package had been flexed, the ingredient is targeted to cover the exterior surface of the delivery vehicle (e.g., in this case, condom 11a). Thereafter, the container 11b separates from the condom 11a and the condom 11a becomes automatically oriented so that its external side administers the ingredient to the area or tissues meant to be thus treated. In this manner, other contact with the ingredient and/or tissues is avoided.

In an alternate embodiment, the reservoir 11c containing the active ingredient is manufactured so that its periphery attached to the walls of the container 11b is also frangible or it may be configured so that perforations across its center more easily become ruptured by the flexing action.

In an alternate embodiment, instead of the flexure of container 11b, direct contact of a finger, digit, penis, or an application wand is inserted through the mouth 11x and used to puncture membrane 11h.

The mouth 11x may be covered by a separate protective over-membrane used to maintain the cleanliness of the container during transit and storage and which would be removed or separately penetrated immediately prior to use.

Figure 6:
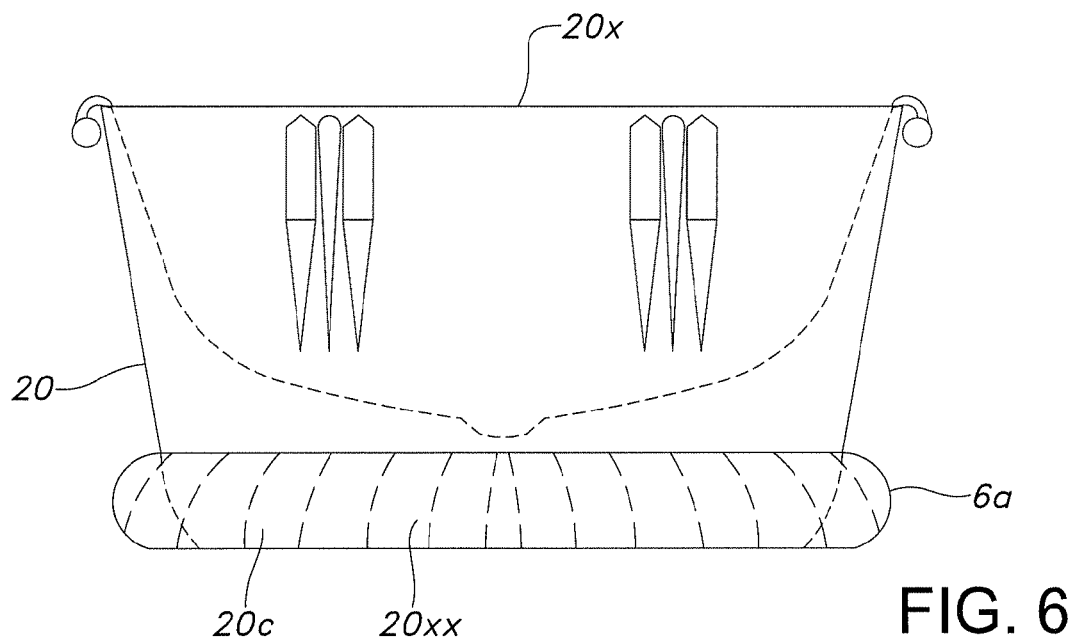
FIG. 6 is a front view of an alternate embodiment of the condom package.
Figure 7:
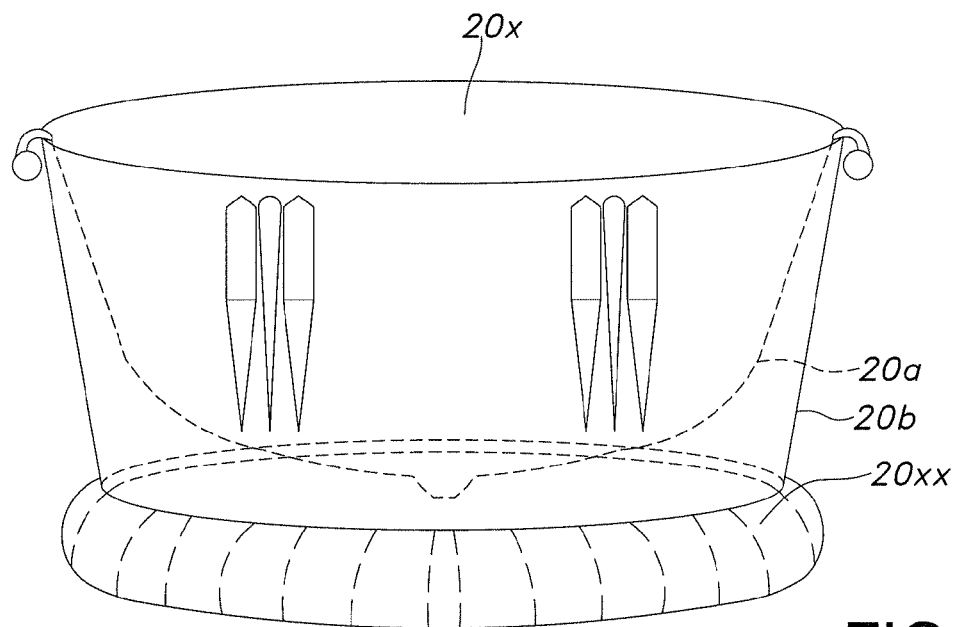
FIG. 7 is a perspective view of the embodiment FIG. 6.

In the embodiment illustrated in FIG. 6 and FIG. 7, a slightly different container 20 is shown that includes a container having a frustoconical shape opened at both ends 20x, 20xx. This container takes less space then the container of FIGS. 1-5. pa Reservoir 20c is attached to the container 20b as shown and it forms a closure for the end 20xx. When the container is applied to a penis to deposit the condom 20a thereon, the walls of the reservoir 20c rupture and deposit the ingredients stored in the reservoir 20c. A seal is used to attach the reservoir 20c to the container 20b, the seal being structured and arranged so that it has a peal strength that is at least 5 times as strong as needed to perforate the reservoir walls thus assuring that the active ingredient is much more likely to spread onto the target vehicle (e.g. the condom) then the external walls of the container.

All seals, perforations, shall be measured for consistency of rupture so as to permit the active ingredient to cover the target vehicle as the package may be affected by varying storage or transit environments with such test parameters to be guided by the ASTM standards for latex condoms D 3492-06.

Figures 8, 10:
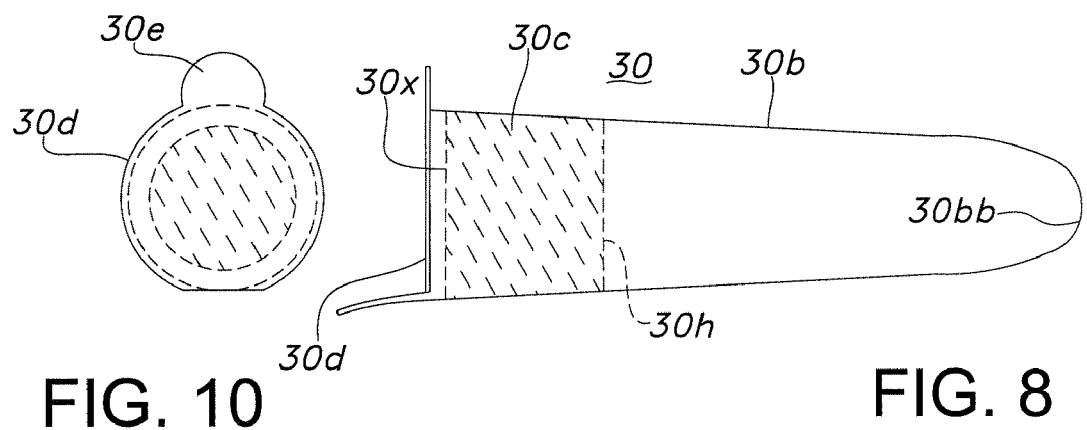
FIG. 8 is a side view of an alternate embodiment of the garment container.
FIG. 10 is a back view of the embodiment of FIG. 8.
Figure 9:
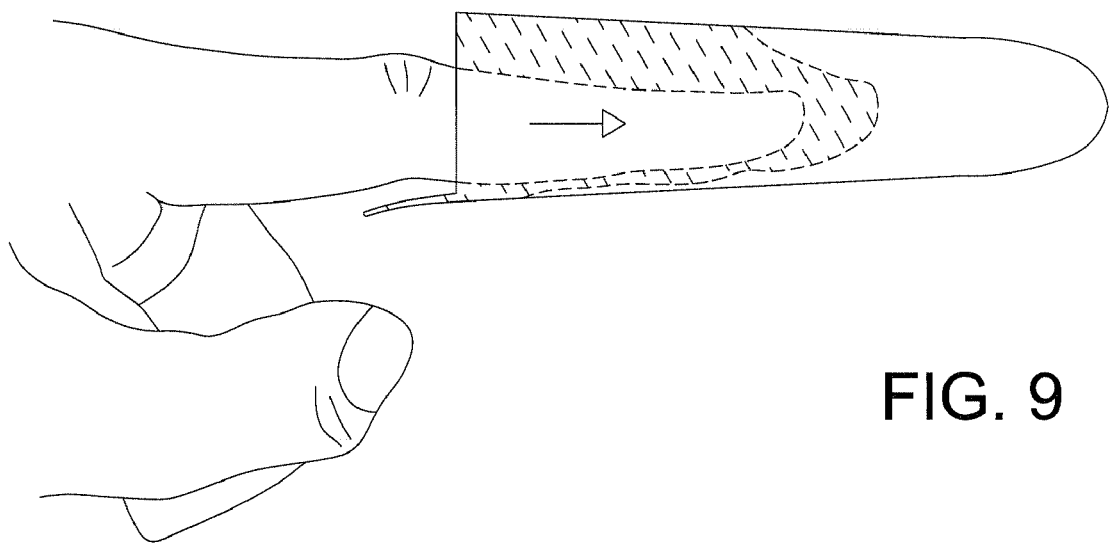
FIG. 9 is a side view of the embodiment of FIG. 8 with a finger inserted.

FIGS. 8-10 show another embodiment of the invention. In this embodiment, a container 30 is provided formed of a conical enclosure 30b having a rounded closed end 30bb. Near open mouth 30z, the container includes a reservoir 30c filled with a suitable fluid. The container is closed with a cover 30d. The cover 30d is frictionally fit into the closure 30b and has a tab 30e that facilitates the removal of the cover from the enclosure. (Similar covers may be used for the embodiments of FIGS. 1-7). Once the cover 30d is removed, a user can stick his finger into the reservoir and push it all the way in, as shown in FIG. 9 thereby rupturing the membrane 30h forming the back wall of the reservoir 30c. The fluid in the reservoir then covers the finger.

Figure 11:
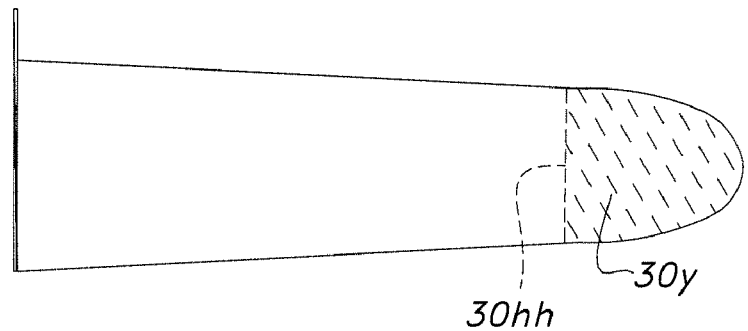
FIG. 11 is a side view of an alternate embodiment of the garment container.
Figure 12:
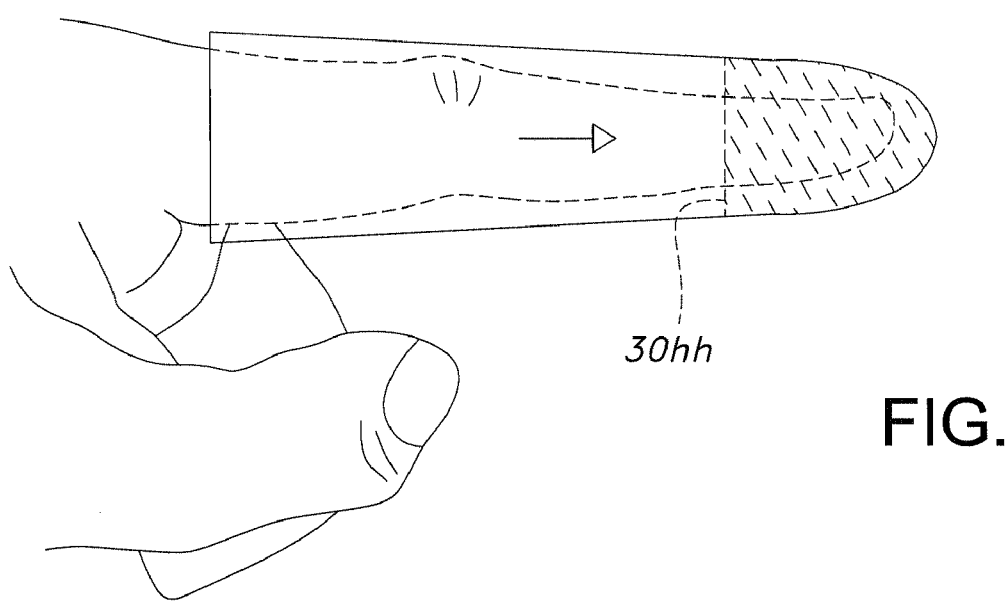
FIG. 12 is a side view of the embodiment of FIG. 11 with a finger inserted.

FIGS. 11 and 12 show an embodiment that is a variation of the embodiment of FIGS. 8-10. In this embodiment the reservoir 30y is placed at the end the enclosure 30b and the finger first pierces the membrane 30hh before it enters the reservoir 30y as shown in FIG. 12.

Figure 13:
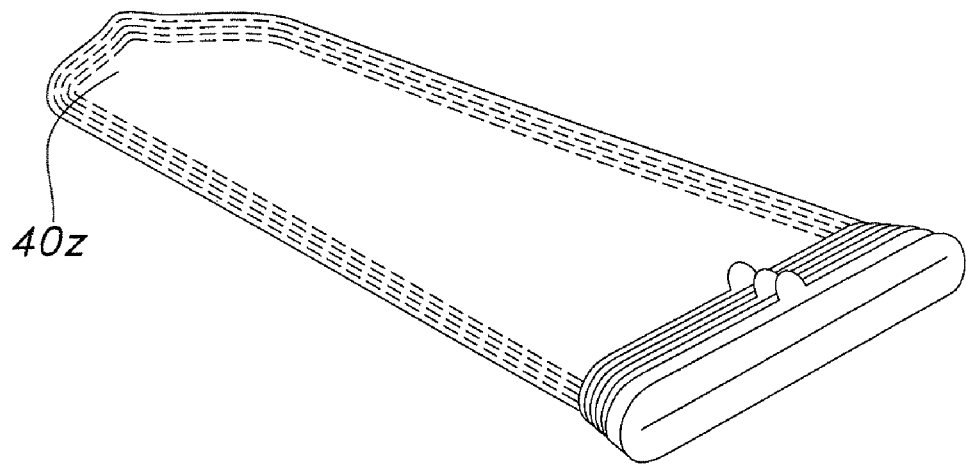
FIG. 13 is a perspective view of a garment dispenser used to dispense several garments, the dispenser being in a closed position.
Figure 14:
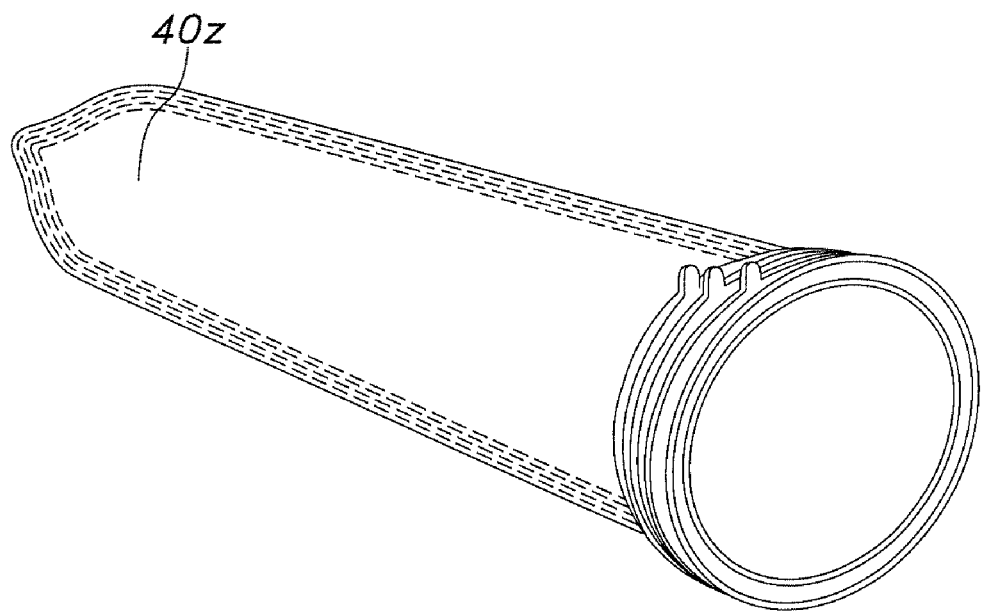
FIG. 14 is a perspective view of the garment dispenser in the opened position.

FIGS. 13 and 14 show yet another embodiment. In this embodiment, the several garment, (that could be condoms, gloves, finger covers and the like) are nested together, each geing formed with its own reservoir 40z. When the appropriate appendage (e.g., finger or penis) is inserted, the reservoir membrane is broken and the contents of the reservoir spread across the surfaces of the appendage.

Figure 16:
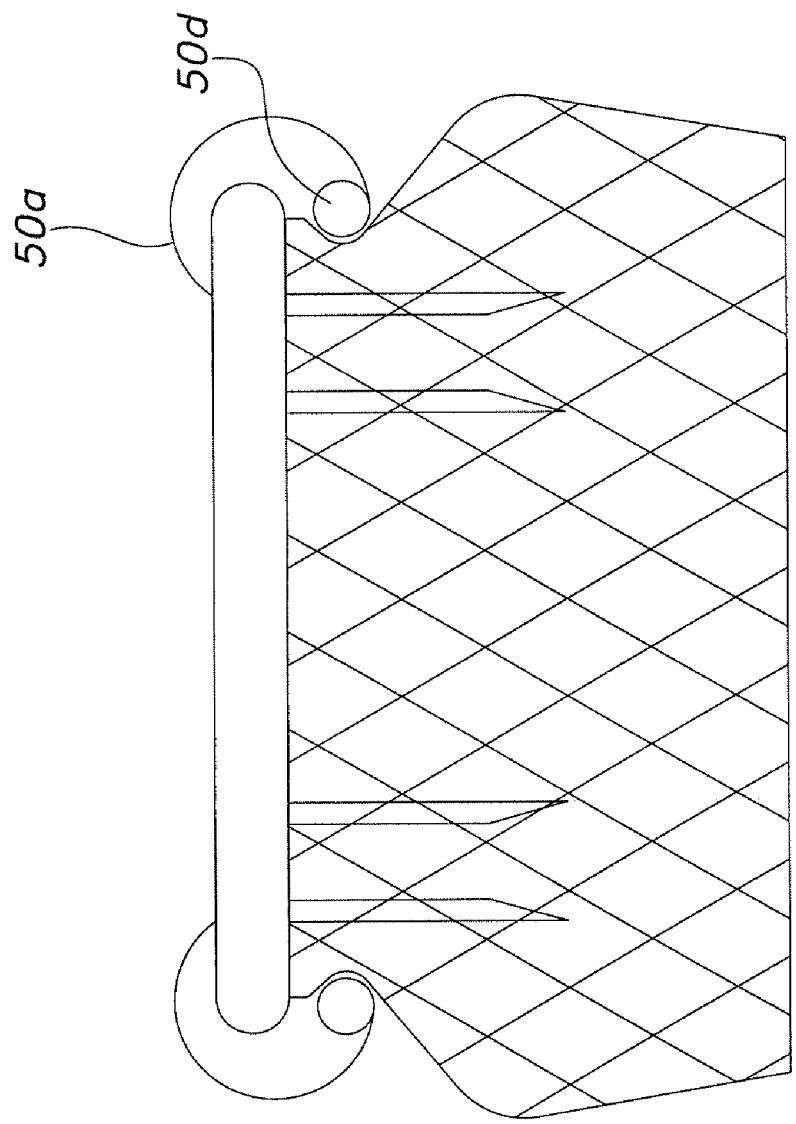
FIG. 16 shows the enclosure of FIG. 15 with a condom therein.

FIGS. 15, 15a and 16 show another embodiment that is a variation of the embodiment of FIGS. 6 and 7. In this embodiment, the container 50b is formed with a mouth 50x and a notch 50t disposed about 4 mm below the mouth. The container 50b is sized and shaped so that the lateral dimension W is about 1 mm smaller then the flat dimension of the condom 50a being stored in the container 50b. Like in the previous embodiments, a portion of the condom 50a is disposed within the enclosure 50b, and the rest is rolled up in a ring. In this case the ring is resting in the notch 50t. Because of distance W, the condom is not stressed while it is disposed in and about the enclosure 50b and will not degrade over time. Of course this embodiment also includes a reservoir 53 as well.

Numerous modifications may be made to this invention without departing from its scope as defined in the appended claims.

What is claimed is:

1. A container comprising:
    an enclosure having a substantially conical sidewall, a first end that is opened and a second end, said enclosure being shaped into a closed configuration in which said enclosure is flat with two lateral edges, and wherein said lateral edges are flexible and transition between said closed configuration and an open configuration;
    a condom having a first portion disposed within said enclosure, and a second portion being rolled up into a toroidal body, said toroidal body being disposed about said first end; and
    a reservoir disposed at said second end and has a membrane, said reservoir being filled with a fluid, said reservoir being positioned such that said membrane ruptures allowing said fluid to be released from said reservoir when said enclosure transitions from said closed to said open configuration.

2. The container of claim 1 wherein said enclosure has a rounded wall closing said second end, said reservoir being formed at least partially by said rounded wall.

3. The container of claim 1 wherein said condom has a free end disposed in said container and another portion rolled up around said first end.

4. The container of claim 1 wherein the reservoir is separated from the condom.

5. The container of claim 1 wherein the reservoir includes two weakened regions capable of being pierced.

6. A condom package comprising:
    a container having a generally tubular body with first and second ends, said first end being opened, said container being formed with two fold lines disposed generally axially along an external surface thereof, said container being folded along said folded lines to form a flat configuration, said fold lines being flexible and said container assuming an open configuration when compressed along said fold lines;
    a condom having a first portion disposed within the container and a second portion rolled up to form a torroidal body and disposed circumferentially about said first end; and
    a reservoir filled with a fluid, said reservoir being disposed in said container without contacting said condom and being arranged to rupture and release said fluid when said container assumes said open configuration from said flat configuration.

7. The condom package of claim 6 wherein said container is opened at said second end.

8. The condom package of claim 7 wherein said second end is covered by a protective cap.

9. The condom package of claim 6 wherein said container is closed at said second end.

* * * * *